(12) United States Patent
Vakharia

(10) Patent No.: US 8,337,394 B2
(45) Date of Patent: Dec. 25, 2012

(54) OVERTUBE WITH EXPANDABLE TIP

(75) Inventor: Omar J. Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 816 days.

(21) Appl. No.: 12/243,334

(22) Filed: Oct. 1, 2008

(65) Prior Publication Data

US 2010/0081877 A1 Apr. 1, 2010

(51) Int. Cl.
*A61B 1/00* (2006.01)
*A61B 17/34* (2006.01)

(52) U.S. Cl. ........................ 600/114; 606/185

(58) Field of Classification Search ............... 600/114, 600/125, 129, 133, 135, 153, 156, 158, 159; 604/28, 36, 37, 110, 517; 606/159, 167, 606/170, 180, 182, 183, 185
See application file for complete search history.

(56) References Cited

U.S. PATENT DOCUMENTS

| | | | |
|---|---|---|---|
| 645,576 A | 3/1900 | Telsa | |
| 649,621 A | 5/1900 | Tesla | |
| 787,412 A | 4/1905 | Tesla | |
| 1,127,948 A | 2/1915 | Wappler | |
| 1,482,653 A | 2/1924 | Lilly | |
| 1,625,602 A | 4/1927 | Gould et al. | |
| 2,028,635 A | 1/1936 | Wappler | |
| 2,031,682 A | 2/1936 | Wappler et al. | |
| 2,113,246 A | 4/1938 | Wappler | |
| 2,155,365 A | 4/1939 | Rankin | |
| 2,191,858 A | 2/1940 | Moore | |
| 2,196,620 A | 4/1940 | Attarian | |
| 2,388,137 A | 10/1945 | Graumlich | |
| 2,493,108 A | 1/1950 | Casey, Jr. | |
| 2,504,152 A | 4/1950 | Riker et al. | |
| 2,938,382 A | 5/1960 | De Graaf | |
| 2,952,206 A | 9/1960 | Becksted | |
| 3,069,195 A | 12/1962 | Buck | |
| 3,170,471 A | 2/1965 | Schnitzer | |
| 3,435,824 A | 4/1969 | Gamponia | |
| 3,470,876 A | 10/1969 | Barchilon | |
| 3,595,239 A | 7/1971 | Petersen | |
| 3,669,487 A | 6/1972 | Roberts et al. | |
| 3,746,881 A | 7/1973 | Fitch et al. | |
| 3,799,672 A | 3/1974 | Vurek | |
| 3,854,473 A | 12/1974 | Matsuo | |

(Continued)

FOREIGN PATENT DOCUMENTS

AU 666310 B2 2/1996

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Thomas J Sweet
*Assistant Examiner* — Kevin G Barry, III

(57) ABSTRACT

An endoscopic overtube with articulating fingers extending from the distal end. The articulating fingers form an opening that may be expanded by a balloon. When positioned in a puncture site in a tissue wall, the articulating fingers dilate and enlarge the puncture site to allow for the body of the overtube to pass through the puncture site. In various embodiments, the fingers may further comprise cutting elements to assist in the dilation of the puncture site.

17 Claims, 8 Drawing Sheets

U.S. PATENT DOCUMENTS

| | | |
|---|---|---|
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |

| | | | | | |
|---|---|---|---|---|---|
| 5,443,463 A | 8/1995 | Stern et al. | 5,690,660 A | 11/1997 | Kauker et al. |
| 5,445,638 A | 8/1995 | Rydell et al. | 5,695,448 A | 12/1997 | Kimura et al. |
| 5,449,021 A | 9/1995 | Chikama | 5,695,505 A | 12/1997 | Yoon |
| 5,456,667 A | 10/1995 | Ham et al. | 5,695,511 A | 12/1997 | Cano et al. |
| 5,456,684 A | 10/1995 | Schmidt et al. | 5,700,275 A | 12/1997 | Bell et al. |
| 5,458,131 A | 10/1995 | Wilk | 5,702,438 A | 12/1997 | Avitall |
| 5,458,583 A | 10/1995 | McNeely et al. | 5,704,892 A | 1/1998 | Adair |
| 5,460,168 A | 10/1995 | Masubuchi et al. | 5,709,708 A | 1/1998 | Thal |
| 5,460,629 A | 10/1995 | Shlain et al. | 5,716,326 A | 2/1998 | Dannan |
| 5,462,561 A | 10/1995 | Voda | 5,730,740 A | 3/1998 | Wales et al. |
| 5,465,731 A | 11/1995 | Bell et al. | 5,735,849 A | 4/1998 | Baden et al. |
| 5,467,763 A | 11/1995 | McMahon et al. | 5,741,234 A | 4/1998 | Aboul-Hosn |
| 5,468,250 A | 11/1995 | Paraschac et al. | 5,741,278 A | 4/1998 | Stevens |
| 5,470,308 A | 11/1995 | Edwards et al. | 5,741,285 A | 4/1998 | McBrayer et al. |
| 5,470,320 A | 11/1995 | Tiefenbrun et al. | 5,746,759 A | 5/1998 | Meade et al. |
| 5,478,347 A | 12/1995 | Aranyi | 5,749,881 A | 5/1998 | Sackier et al. |
| 5,480,404 A | 1/1996 | Kammerer et al. | 5,749,889 A | 5/1998 | Bacich et al. |
| 5,482,054 A | 1/1996 | Slater et al. | 5,752,951 A | 5/1998 | Yanik |
| 5,484,451 A | 1/1996 | Akopov et al. | 5,755,731 A | 5/1998 | Grinberg |
| 5,489,256 A | 2/1996 | Adair | 5,766,167 A | 6/1998 | Eggers et al. |
| 5,496,347 A | 3/1996 | Hashiguchi et al. | 5,766,170 A | 6/1998 | Eggers |
| 5,499,990 A | 3/1996 | Schülken et al. | 5,766,205 A | 6/1998 | Zvenyatsky et al. |
| 5,499,992 A | 3/1996 | Meade et al. | 5,769,849 A | 6/1998 | Eggers |
| 5,501,692 A | 3/1996 | Riza | 5,779,701 A | 7/1998 | McBrayer et al. |
| 5,503,616 A | 4/1996 | Jones | 5,779,716 A | 7/1998 | Cano et al. |
| 5,505,686 A | 4/1996 | Willis et al. | 5,779,727 A | 7/1998 | Orejola |
| 5,507,755 A | 4/1996 | Gresl et al. | 5,782,859 A | 7/1998 | Nicholas et al. |
| 5,511,564 A | 4/1996 | Wilk | 5,782,866 A | 7/1998 | Wenstrom, Jr. |
| 5,514,157 A | 5/1996 | Nicholas et al. | 5,791,022 A | 8/1998 | Bohman |
| 5,522,829 A | 6/1996 | Michalos | 5,792,113 A | 8/1998 | Kramer et al. |
| 5,522,830 A | 6/1996 | Aranyi | 5,792,153 A | 8/1998 | Swain et al. |
| 5,527,321 A | 6/1996 | Hinchliffe | 5,792,165 A | 8/1998 | Klieman et al. |
| 5,536,248 A | 7/1996 | Weaver et al. | 5,797,835 A | 8/1998 | Green |
| 5,538,509 A * | 7/1996 | Dunlap et al. ................ 604/264 | 5,797,928 A | 8/1998 | Kogasaka |
| 5,540,648 A | 7/1996 | Yoon | 5,797,939 A | 8/1998 | Yoon |
| 5,554,151 A | 9/1996 | Hinchliffe | 5,797,941 A | 8/1998 | Schulze et al. |
| 5,555,883 A | 9/1996 | Avitall | 5,803,903 A | 9/1998 | Athas et al. |
| 5,558,133 A | 9/1996 | Bortoli et al. | 5,808,665 A | 9/1998 | Green |
| 5,562,693 A | 10/1996 | Devlin et al. | 5,810,806 A | 9/1998 | Ritchart et al. |
| 5,569,243 A | 10/1996 | Kortenbach et al. | 5,810,849 A | 9/1998 | Kontos |
| 5,569,298 A | 10/1996 | Schnell | 5,810,865 A | 9/1998 | Koscher et al. |
| 5,573,540 A | 11/1996 | Yoon | 5,810,876 A | 9/1998 | Kelleher |
| 5,578,030 A | 11/1996 | Levin | 5,810,877 A | 9/1998 | Roth et al. |
| 5,582,611 A | 12/1996 | Tsuruta et al. | 5,813,976 A | 9/1998 | Filipi et al. |
| 5,582,617 A | 12/1996 | Klieman et al. | 5,814,058 A | 9/1998 | Carlson et al. |
| 5,584,845 A | 12/1996 | Hart | 5,817,061 A | 10/1998 | Goodwin et al. |
| 5,591,179 A | 1/1997 | Edelstein | 5,817,107 A | 10/1998 | Schaller |
| 5,593,420 A | 1/1997 | Eubanks, Jr. et al. | 5,817,119 A | 10/1998 | Klieman et al. |
| 5,595,562 A | 1/1997 | Grier | 5,819,736 A | 10/1998 | Avny et al. |
| 5,597,378 A | 1/1997 | Jervis | 5,824,071 A | 10/1998 | Nelson et al. |
| 5,601,573 A | 2/1997 | Fogelberg et al. | 5,827,281 A | 10/1998 | Levin |
| 5,601,588 A | 2/1997 | Tonomura et al. | 5,827,299 A | 10/1998 | Thomason et al. |
| 5,604,531 A | 2/1997 | Iddan et al. | 5,830,231 A | 11/1998 | Geiges, Jr. |
| 5,607,389 A | 3/1997 | Edwards et al. | 5,833,700 A | 11/1998 | Fogelberg et al. |
| 5,607,450 A | 3/1997 | Zvenyatsky et al. | 5,833,703 A | 11/1998 | Manushakian |
| 5,613,975 A | 3/1997 | Christy | 5,843,017 A | 12/1998 | Yoon |
| 5,618,303 A | 4/1997 | Marlow et al. | 5,843,121 A | 12/1998 | Yoon |
| 5,620,415 A | 4/1997 | Lucey et al. | 5,849,022 A | 12/1998 | Sakashita et al. |
| 5,624,399 A | 4/1997 | Ackerman | 5,853,374 A | 12/1998 | Hart et al. |
| 5,624,431 A | 4/1997 | Gerry et al. | 5,855,585 A | 1/1999 | Kontos |
| 5,626,578 A | 5/1997 | Tihon | 5,860,913 A | 1/1999 | Yamaya et al. |
| 5,628,732 A | 5/1997 | Antoon, Jr. et al. | 5,860,995 A | 1/1999 | Berkelaar |
| 5,630,782 A | 5/1997 | Adair | 5,868,762 A | 2/1999 | Cragg et al. |
| 5,643,283 A | 7/1997 | Younker | 5,876,411 A | 3/1999 | Kontos |
| 5,643,292 A | 7/1997 | Hart | 5,882,331 A | 3/1999 | Sasaki |
| 5,643,294 A | 7/1997 | Tovey et al. | 5,882,344 A | 3/1999 | Stouder, Jr. |
| 5,644,798 A | 7/1997 | Shah | 5,893,846 A | 4/1999 | Bales et al. |
| 5,645,083 A | 7/1997 | Essig et al. | 5,893,874 A | 4/1999 | Bourque et al. |
| 5,645,565 A | 7/1997 | Rudd et al. | 5,893,875 A | 4/1999 | O'Connor et al. |
| 5,649,372 A | 7/1997 | Souza | 5,899,919 A | 5/1999 | Eubanks, Jr. et al. |
| 5,653,677 A | 8/1997 | Okada et al. | 5,902,254 A | 5/1999 | Magram |
| 5,653,690 A | 8/1997 | Booth et al. | 5,904,702 A | 5/1999 | Ek et al. |
| 5,653,722 A | 8/1997 | Kieturakis | 5,908,420 A | 6/1999 | Parins et al. |
| 5,662,663 A | 9/1997 | Shallman | 5,908,429 A | 6/1999 | Yoon |
| 5,669,875 A | 9/1997 | van Eerdenburg | 5,911,737 A | 6/1999 | Lee et al. |
| 5,681,324 A | 10/1997 | Kammerer et al. | 5,916,147 A | 6/1999 | Boury |
| 5,681,330 A | 10/1997 | Hughett et al. | 5,921,993 A | 7/1999 | Yoon |
| 5,685,820 A | 11/1997 | Riek et al. | 5,921,997 A | 7/1999 | Fogelberg et al. |
| 5,690,656 A | 11/1997 | Cope et al. | 5,922,008 A | 7/1999 | Gimpelson |

| Patent | | Date | Inventor |
|---|---|---|---|
| 5,925,052 | A | 7/1999 | Simmons |
| 5,928,255 | A | 7/1999 | Meade et al. |
| 5,928,266 | A | 7/1999 | Kontos |
| 5,936,536 | A | 8/1999 | Morris |
| 5,944,718 | A | 8/1999 | Austin et al. |
| 5,951,549 | A | 9/1999 | Richardson et al. |
| 5,954,720 | A | 9/1999 | Wilson et al. |
| 5,954,731 | A | 9/1999 | Yoon |
| 5,957,943 | A | 9/1999 | Vaitekunas |
| 5,957,953 | A | 9/1999 | DiPoto et al. |
| 5,971,995 | A | 10/1999 | Rousseau |
| 5,972,002 | A | 10/1999 | Bark et al. |
| 5,976,074 | A | 11/1999 | Moriyama |
| 5,976,075 | A | 11/1999 | Beane et al. |
| 5,976,130 | A | 11/1999 | McBrayer et al. |
| 5,976,131 | A | 11/1999 | Guglielmi et al. |
| 5,980,539 | A | 11/1999 | Kontos |
| 5,980,556 | A | 11/1999 | Giordano et al. |
| 5,984,938 | A | 11/1999 | Yoon |
| 5,984,939 | A | 11/1999 | Yoon |
| 5,989,182 | A | 11/1999 | Hori et al. |
| 5,993,447 | A | 11/1999 | Blewett et al. |
| 5,997,555 | A | 12/1999 | Kontos |
| 6,001,120 | A | 12/1999 | Levin |
| 6,004,269 | A | 12/1999 | Crowley et al. |
| 6,004,330 | A | 12/1999 | Middleman et al. |
| 6,007,566 | A | 12/1999 | Wenstrom, Jr. |
| 6,010,515 | A | 1/2000 | Swain et al. |
| 6,012,494 | A | 1/2000 | Balazs |
| 6,017,356 | A * | 1/2000 | Frederick et al. ............ 606/185 |
| 6,019,770 | A | 2/2000 | Christoudias |
| 6,024,708 | A | 2/2000 | Bales et al. |
| 6,024,747 | A | 2/2000 | Kontos |
| 6,027,522 | A | 2/2000 | Palmer |
| 6,030,365 | A | 2/2000 | Laufer |
| 6,030,634 | A | 2/2000 | Wu et al. |
| 6,033,399 | A | 3/2000 | Gines |
| 6,036,685 | A | 3/2000 | Mueller |
| 6,053,927 | A | 4/2000 | Hamas |
| 6,066,160 | A | 5/2000 | Colvin et al. |
| 6,068,603 | A | 5/2000 | Suzuki |
| 6,068,629 | A | 5/2000 | Haissaguerre et al. |
| 6,071,233 | A | 6/2000 | Ishikawa et al. |
| 6,074,408 | A | 6/2000 | Freeman |
| 6,086,530 | A | 7/2000 | Mack |
| 6,090,108 | A | 7/2000 | McBrayer et al. |
| 6,096,046 | A | 8/2000 | Weiss |
| 6,102,926 | A | 8/2000 | Tartaglia et al. |
| 6,106,473 | A | 8/2000 | Violante et al. |
| 6,109,852 | A | 8/2000 | Shahinpoor et al. |
| 6,110,154 | A | 8/2000 | Shimomura et al. |
| 6,110,183 | A | 8/2000 | Cope |
| 6,113,593 | A | 9/2000 | Tu et al. |
| 6,117,144 | A | 9/2000 | Nobles et al. |
| 6,117,158 | A | 9/2000 | Measamer et al. |
| 6,139,555 | A | 10/2000 | Hart et al. |
| 6,146,391 | A | 11/2000 | Cigaina |
| 6,148,222 | A | 11/2000 | Ramsey, III |
| 6,149,653 | A | 11/2000 | Deslauriers |
| 6,149,662 | A | 11/2000 | Pugliesi et al. |
| 6,156,006 | A | 12/2000 | Brosens et al. |
| 6,159,200 | A | 12/2000 | Verdura et al. |
| 6,165,184 | A | 12/2000 | Verdura et al. |
| 6,168,570 | B1 | 1/2001 | Ferrera |
| 6,168,605 | B1 | 1/2001 | Measamer et al. |
| 6,170,130 | B1 | 1/2001 | Hamilton et al. |
| 6,179,776 | B1 | 1/2001 | Adams et al. |
| 6,179,837 | B1 | 1/2001 | Hooven |
| 6,183,420 | B1 | 2/2001 | Douk et al. |
| 6,190,353 | B1 | 2/2001 | Makower et al. |
| 6,190,384 | B1 | 2/2001 | Ouchi |
| 6,190,399 | B1 | 2/2001 | Palmer et al. |
| 6,203,533 | B1 | 3/2001 | Ouchi |
| 6,206,872 | B1 | 3/2001 | Lafond et al. |
| 6,206,877 | B1 | 3/2001 | Kese et al. |
| 6,214,007 | B1 | 4/2001 | Anderson |
| 6,228,096 | B1 | 5/2001 | Marchand |
| 6,234,958 | B1 | 5/2001 | Snoke et al. |
| 6,245,079 | B1 | 6/2001 | Nobles et al. |
| 6,246,914 | B1 | 6/2001 | de la Rama et al. |
| 6,258,064 | B1 | 7/2001 | Smith et al. |
| 6,261,242 | B1 | 7/2001 | Roberts et al. |
| 6,264,664 | B1 | 7/2001 | Avellanet |
| 6,270,497 | B1 | 8/2001 | Sekino et al. |
| 6,270,505 | B1 | 8/2001 | Yoshida et al. |
| 6,277,136 | B1 | 8/2001 | Bonutti |
| 6,283,963 | B1 | 9/2001 | Regula |
| 6,293,909 | B1 | 9/2001 | Chu et al. |
| 6,293,952 | B1 | 9/2001 | Brosens et al. |
| 6,296,630 | B1 | 10/2001 | Altman et al. |
| 6,322,578 | B1 | 11/2001 | Houle et al. |
| 6,326,177 | B1 | 12/2001 | Schoenbach et al. |
| 6,328,730 | B1 | 12/2001 | Harkrider, Jr. |
| 6,350,267 | B1 | 2/2002 | Stefanchik |
| 6,350,278 | B1 | 2/2002 | Lenker et al. |
| 6,352,503 | B1 | 3/2002 | Matsui et al. |
| 6,352,543 | B1 | 3/2002 | Cole |
| 6,355,035 | B1 | 3/2002 | Manushakian |
| 6,361,534 | B1 | 3/2002 | Chen et al. |
| 6,371,956 | B1 | 4/2002 | Wilson et al. |
| 6,379,366 | B1 | 4/2002 | Fleischman et al. |
| 6,383,195 | B1 | 5/2002 | Richard |
| 6,383,197 | B1 | 5/2002 | Conlon et al. |
| 6,391,029 | B1 | 5/2002 | Hooven et al. |
| 6,402,735 | B1 | 6/2002 | Langevin |
| 6,406,440 | B1 | 6/2002 | Stefanchik |
| 6,409,727 | B1 | 6/2002 | Bales et al. |
| 6,409,733 | B1 | 6/2002 | Conlon et al. |
| 6,427,089 | B1 | 7/2002 | Knowlton |
| 6,431,500 | B1 | 8/2002 | Jacobs et al. |
| 6,443,970 | B1 | 9/2002 | Schulze et al. |
| 6,443,988 | B2 | 9/2002 | Felt et al. |
| 6,447,511 | B1 | 9/2002 | Slater |
| 6,447,523 | B1 | 9/2002 | Middleman et al. |
| 6,454,783 | B1 | 9/2002 | Piskun |
| 6,454,785 | B2 | 9/2002 | De Hoyos Garza |
| 6,458,076 | B1 | 10/2002 | Pruitt |
| 6,464,701 | B1 | 10/2002 | Hooven et al. |
| 6,464,702 | B2 | 10/2002 | Schulze et al. |
| 6,475,104 | B1 | 11/2002 | Lutz et al. |
| 6,485,411 | B1 | 11/2002 | Konstorum et al. |
| 6,489,745 | B1 | 12/2002 | Koreis |
| 6,491,626 | B1 | 12/2002 | Stone et al. |
| 6,491,627 | B1 | 12/2002 | Komi |
| 6,491,691 | B1 | 12/2002 | Morley et al. |
| 6,493,590 | B1 | 12/2002 | Wessman et al. |
| 6,494,893 | B2 | 12/2002 | Dubrul et al. |
| 6,500,176 | B1 | 12/2002 | Truckai et al. |
| 6,503,192 | B1 | 1/2003 | Ouchi |
| 6,506,190 | B1 | 1/2003 | Walshe |
| 6,508,827 | B1 | 1/2003 | Manhes |
| 6,514,239 | B2 | 2/2003 | Shimmura et al. |
| 6,520,954 | B2 | 2/2003 | Ouchi |
| 6,543,456 | B1 | 4/2003 | Freeman |
| 6,551,270 | B1 | 4/2003 | Bimbo et al. |
| 6,554,829 | B2 | 4/2003 | Schulze et al. |
| 6,558,384 | B2 | 5/2003 | Mayenberger |
| 6,562,035 | B1 | 5/2003 | Levin |
| 6,562,052 | B2 | 5/2003 | Nobles et al. |
| 6,569,159 | B1 | 5/2003 | Edwards et al. |
| 6,572,629 | B2 | 6/2003 | Kalloo et al. |
| 6,572,635 | B1 | 6/2003 | Bonutti |
| 6,575,988 | B2 | 6/2003 | Rousseau |
| 6,579,311 | B1 | 6/2003 | Makower |
| 6,585,642 | B2 | 7/2003 | Christopher |
| 6,585,717 | B1 | 7/2003 | Wittenberger et al. |
| 6,587,750 | B2 | 7/2003 | Gerbi et al. |
| 6,592,559 | B1 | 7/2003 | Pakter et al. |
| 6,592,603 | B2 | 7/2003 | Lasner |
| 6,602,262 | B2 | 8/2003 | Griego et al. |
| 6,605,105 | B1 | 8/2003 | Cuschieri et al. |
| 6,610,072 | B1 | 8/2003 | Christy et al. |
| 6,610,074 | B2 | 8/2003 | Santilli |
| 6,620,193 | B1 | 9/2003 | Lau et al. |
| 6,623,448 | B2 | 9/2003 | Slater |
| 6,626,919 | B1 | 9/2003 | Swanstrom |
| 6,632,229 | B1 | 10/2003 | Yamanouchi |
| 6,638,286 | B1 | 10/2003 | Burbank et al. |

| | | |
|---|---|---|
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,776,787 B2 * | 8/2004 | Phung et al. ............ 606/185 |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,152,488 B2 | 12/2006 | Hedrich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francese et al. |
| 7,232,414 B2 | 6/2007 | Gonzalez |

| Patent | Date | Inventor |
|---|---|---|
| 7,232,445 B2 | 6/2007 | Kortenbach et al. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,674,259 B2 | 3/2010 | Shadduck |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,758,577 B2 | 7/2010 | Nobis et al. |
| 7,762,949 B2 | 7/2010 | Nakao |
| 7,762,998 B2 | 7/2010 | Birk et al. |
| 7,771,416 B2 | 8/2010 | Spivey et al. |
| 7,780,683 B2 | 8/2010 | Roue et al. |
| 7,780,691 B2 | 8/2010 | Stefanchik |
| 7,794,409 B2 | 9/2010 | Damarati |
| 7,794,475 B2 | 9/2010 | Hess et al. |
| 7,828,186 B2 | 11/2010 | Wales |
| 7,837,615 B2 | 11/2010 | Le et al. |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,988,685 B2 | 8/2011 | Ziaie et al. |
| 8,029,504 B2 | 10/2011 | Long |
| 8,037,591 B2 | 10/2011 | Spivey et al. |
| 8,075,587 B2 | 12/2011 | Ginn |
| 8,088,062 B2 | 1/2012 | Zwolinski |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1* | 3/2002 | Bonutti .................. 606/170 |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0206859 A1 | 10/2004 | Chong et al. |

| | | | | | | |
|---|---|---|---|---|---|---|
| 2004/0210245 A1 | 10/2004 | Erickson et al. | | 2005/0277957 A1 | 12/2005 | Kuhns et al. |
| 2004/0215058 A1 | 10/2004 | Zirps et al. | | 2005/0283118 A1 | 12/2005 | Uth et al. |
| 2004/0225183 A1 | 11/2004 | Michlitsch et al. | | 2005/0283119 A1 | 12/2005 | Uth et al. |
| 2004/0225186 A1 | 11/2004 | Horne, Jr. et al. | | 2005/0288555 A1 | 12/2005 | Binmoeller |
| 2004/0230095 A1 | 11/2004 | Stefanchik et al. | | 2006/0004406 A1 | 1/2006 | Wehrstein et al. |
| 2004/0230096 A1 | 11/2004 | Stefanchik et al. | | 2006/0004409 A1 | 1/2006 | Nobis et al. |
| 2004/0230097 A1 | 11/2004 | Stefanchik et al. | | 2006/0004410 A1 | 1/2006 | Nobis et al. |
| 2004/0230161 A1 | 11/2004 | Zeiner | | 2006/0015009 A1 | 1/2006 | Jaffe et al. |
| 2004/0249246 A1 | 12/2004 | Campos | | 2006/0020167 A1 | 1/2006 | Sitzmann |
| 2004/0249367 A1 | 12/2004 | Saadat et al. | | 2006/0020247 A1 | 1/2006 | Kagan et al. |
| 2004/0249394 A1 | 12/2004 | Morris et al. | | 2006/0025654 A1 | 2/2006 | Suzuki et al. |
| 2004/0249443 A1 | 12/2004 | Shanley et al. | | 2006/0025781 A1 | 2/2006 | Young et al. |
| 2005/0004515 A1 | 1/2005 | Hart et al. | | 2006/0025812 A1 | 2/2006 | Shelton, IV |
| 2005/0033265 A1 | 2/2005 | Engel et al. | | 2006/0025819 A1 | 2/2006 | Nobis et al. |
| 2005/0033277 A1 | 2/2005 | Clague et al. | | 2006/0036267 A1 | 2/2006 | Saadat et al. |
| 2005/0033319 A1 | 2/2005 | Gambale et al. | | 2006/0041188 A1 | 2/2006 | Dirusso et al. |
| 2005/0033333 A1 | 2/2005 | Smith et al. | | 2006/0058582 A1 | 3/2006 | Maahs et al. |
| 2005/0043690 A1 | 2/2005 | Todd | | 2006/0058776 A1 | 3/2006 | Bilsbury |
| 2005/0049616 A1 | 3/2005 | Rivera et al. | | 2006/0069396 A1 | 3/2006 | Meade et al. |
| 2005/0065397 A1 | 3/2005 | Saadat et al. | | 2006/0069424 A1 | 3/2006 | Acosta et al. |
| 2005/0065517 A1 | 3/2005 | Chin | | 2006/0069425 A1 | 3/2006 | Hillis et al. |
| 2005/0070754 A1 | 3/2005 | Nobis et al. | | 2006/0074413 A1 | 4/2006 | Behzadian |
| 2005/0070763 A1 | 3/2005 | Nobis et al. | | 2006/0079890 A1 | 4/2006 | Guerra |
| 2005/0070764 A1 | 3/2005 | Nobis et al. | | 2006/0089528 A1 | 4/2006 | Tartaglia et al. |
| 2005/0080413 A1 | 4/2005 | Canady | | 2006/0095031 A1 | 5/2006 | Ormsby |
| 2005/0085693 A1 | 4/2005 | Belson et al. | | 2006/0095060 A1 | 5/2006 | Mayenberger et al. |
| 2005/0085832 A1 | 4/2005 | Sancoff et al. | | 2006/0100687 A1 | 5/2006 | Fahey et al. |
| 2005/0090837 A1 | 4/2005 | Sixto, Jr. et al. | | 2006/0106423 A1 | 5/2006 | Weisel et al. |
| 2005/0090838 A1 | 4/2005 | Sixto, Jr. et al. | | 2006/0111209 A1 | 5/2006 | Hinman et al. |
| 2005/0101837 A1 | 5/2005 | Kalloo et al. | | 2006/0111210 A1 | 5/2006 | Hinman et al. |
| 2005/0101838 A1 | 5/2005 | Camillocci et al. | | 2006/0111704 A1 | 5/2006 | Brenneman et al. |
| 2005/0107663 A1 | 5/2005 | Saadat et al. | | 2006/0129166 A1 | 6/2006 | Lavelle |
| 2005/0107664 A1 | 5/2005 | Kalloo et al. | | 2006/0135962 A1 | 6/2006 | Kick et al. |
| 2005/0110881 A1 | 5/2005 | Glukhovsky et al. | | 2006/0135971 A1 | 6/2006 | Swanstrom et al. |
| 2005/0113847 A1 | 5/2005 | Gadberry et al. | | 2006/0135984 A1 | 6/2006 | Kramer et al. |
| 2005/0119613 A1 | 6/2005 | Moenning et al. | | 2006/0142644 A1 | 6/2006 | Mulac et al. |
| 2005/0124855 A1 | 6/2005 | Jaffe et al. | | 2006/0142652 A1 | 6/2006 | Keenan |
| 2005/0125010 A1 | 6/2005 | Smith et al. | | 2006/0142790 A1 | 6/2006 | Gertner |
| 2005/0131279 A1 | 6/2005 | Boulais et al. | | 2006/0142798 A1 | 6/2006 | Holman et al. |
| 2005/0131457 A1 | 6/2005 | Douglas et al. | | 2006/0149131 A1 | 7/2006 | Or |
| 2005/0137454 A1 | 6/2005 | Saadat et al. | | 2006/0149132 A1 | 7/2006 | Iddan |
| 2005/0143647 A1 | 6/2005 | Minai et al. | | 2006/0149135 A1 | 7/2006 | Paz |
| 2005/0143690 A1 | 6/2005 | High | | 2006/0161190 A1 | 7/2006 | Gadberry et al. |
| 2005/0143774 A1 | 6/2005 | Polo | | 2006/0167416 A1 | 7/2006 | Mathis et al. |
| 2005/0143803 A1 | 6/2005 | Watson et al. | | 2006/0167482 A1 | 7/2006 | Swain et al. |
| 2005/0149078 A1* | 7/2005 | Vargas et al. ............... 606/153 | | 2006/0178560 A1 | 8/2006 | Saadat et al. |
| 2005/0149087 A1 | 7/2005 | Ahlberg et al. | | 2006/0183975 A1 | 8/2006 | Saadat et al. |
| 2005/0149096 A1 | 7/2005 | Hilal et al. | | 2006/0184161 A1 | 8/2006 | Maahs et al. |
| 2005/0159648 A1 | 7/2005 | Freed | | 2006/0189844 A1 | 8/2006 | Tien |
| 2005/0165272 A1 | 7/2005 | Okada et al. | | 2006/0189845 A1 | 8/2006 | Maahs et al. |
| 2005/0165378 A1 | 7/2005 | Heinrich et al. | | 2006/0190027 A1 | 8/2006 | Downey |
| 2005/0165411 A1 | 7/2005 | Orban, III | | 2006/0195084 A1 | 8/2006 | Slater |
| 2005/0165429 A1 | 7/2005 | Douglas et al. | | 2006/0200005 A1 | 9/2006 | Bjork et al. |
| 2005/0182429 A1 | 8/2005 | Yamanouchi | | 2006/0200169 A1 | 9/2006 | Sniffin |
| 2005/0192478 A1 | 9/2005 | Williams et al. | | 2006/0200170 A1 | 9/2006 | Aranyi |
| 2005/0192598 A1 | 9/2005 | Johnson et al. | | 2006/0200199 A1 | 9/2006 | Bonutti et al. |
| 2005/0192602 A1 | 9/2005 | Manzo | | 2006/0217665 A1 | 9/2006 | Prosek |
| 2005/0192654 A1 | 9/2005 | Chanduszko et al. | | 2006/0217697 A1 | 9/2006 | Lau et al. |
| 2005/0209624 A1 | 9/2005 | Vijay | | 2006/0217742 A1 | 9/2006 | Messerly et al. |
| 2005/0215858 A1 | 9/2005 | Vail, III | | 2006/0217743 A1 | 9/2006 | Messerly et al. |
| 2005/0216050 A1 | 9/2005 | Sepetka et al. | | 2006/0229639 A1 | 10/2006 | Whitfield |
| 2005/0228406 A1 | 10/2005 | Bose | | 2006/0229640 A1 | 10/2006 | Whitfield |
| 2005/0234297 A1 | 10/2005 | Devierre et al. | | 2006/0237022 A1 | 10/2006 | Chen et al. |
| 2005/0250983 A1 | 11/2005 | Tremaglio et al. | | 2006/0237023 A1 | 10/2006 | Cox et al. |
| 2005/0250990 A1 | 11/2005 | Le et al. | | 2006/0241570 A1 | 10/2006 | Wilk |
| 2005/0250993 A1 | 11/2005 | Jaeger | | 2006/0247576 A1 | 11/2006 | Poncet |
| 2005/0251166 A1 | 11/2005 | Vaughan et al. | | 2006/0247673 A1 | 11/2006 | Voegele et al. |
| 2005/0251176 A1 | 11/2005 | Swanstrom et al. | | 2006/0253004 A1 | 11/2006 | Frisch et al. |
| 2005/0261674 A1 | 11/2005 | Nobis et al. | | 2006/0253039 A1 | 11/2006 | McKenna et al. |
| 2005/0267492 A1 | 12/2005 | Poncet et al. | | 2006/0258907 A1 | 11/2006 | Stefanchik et al. |
| 2005/0272975 A1 | 12/2005 | McWeeney et al. | | 2006/0258908 A1 | 11/2006 | Stefanchik et al. |
| 2005/0272977 A1 | 12/2005 | Saadat et al. | | 2006/0258910 A1 | 11/2006 | Stefanchik et al. |
| 2005/0273084 A1 | 12/2005 | Hinman et al. | | 2006/0258954 A1 | 11/2006 | Timberlake et al. |
| 2005/0277945 A1 | 12/2005 | Saadat et al. | | 2006/0258955 A1 | 11/2006 | Hoffman et al. |
| 2005/0277951 A1 | 12/2005 | Smith et al. | | 2006/0259010 A1 | 11/2006 | Stefanchik et al. |
| 2005/0277952 A1 | 12/2005 | Arp et al. | | 2006/0264752 A1 | 11/2006 | Rubinsky et al. |
| 2005/0277954 A1 | 12/2005 | Smith et al. | | 2006/0264904 A1 | 11/2006 | Kerby et al. |
| 2005/0277955 A1 | 12/2005 | Palmer et al. | | 2006/0264930 A1 | 11/2006 | Nishimura |
| 2005/0277956 A1 | 12/2005 | Francese et al. | | 2006/0270902 A1 | 11/2006 | Igarashi et al. |

| | | | | | | |
|---|---|---|---|---|---|---|
| 2006/0271102 A1 | 11/2006 | Bosshard et al. | | 2007/0270895 A1 | 11/2007 | Nobis et al. |
| 2006/0276835 A1 | 12/2006 | Uchida | | 2007/0270907 A1 | 11/2007 | Stokes et al. |
| 2006/0281970 A1 | 12/2006 | Stokes et al. | | 2007/0282371 A1 | 12/2007 | Lee et al. |
| 2006/0282106 A1 | 12/2006 | Cole et al. | | 2007/0293727 A1 | 12/2007 | Goldfarb et al. |
| 2006/0285732 A1 | 12/2006 | Horn et al. | | 2007/0299387 A1 | 12/2007 | Williams et al. |
| 2006/0287644 A1 | 12/2006 | Inganas et al. | | 2008/0004650 A1 | 1/2008 | George |
| 2006/0287666 A1 | 12/2006 | Saadat et al. | | 2008/0015409 A1 | 1/2008 | Barlow et al. |
| 2006/0293626 A1 | 12/2006 | Byrum et al. | | 2008/0015552 A1 | 1/2008 | Doyle et al. |
| 2007/0002135 A1 | 1/2007 | Glukhovsky | | 2008/0021416 A1 | 1/2008 | Arai et al. |
| 2007/0005019 A1 | 1/2007 | Okishige | | 2008/0022927 A1 | 1/2008 | Zhang et al. |
| 2007/0010801 A1 | 1/2007 | Chen et al. | | 2008/0027387 A1 | 1/2008 | Grabinsky |
| 2007/0015965 A1 | 1/2007 | Cox et al. | | 2008/0033451 A1 | 2/2008 | Rieber et al. |
| 2007/0016225 A1 | 1/2007 | Nakao | | 2008/0051629 A1 | 2/2008 | Sugiyama et al. |
| 2007/0032700 A1 | 2/2007 | Fowler et al. | | 2008/0051735 A1 | 2/2008 | Measamer et al. |
| 2007/0032701 A1 | 2/2007 | Fowler et al. | | 2008/0058586 A1 | 3/2008 | Karpiel |
| 2007/0043261 A1 | 2/2007 | Watanabe et al. | | 2008/0065169 A1 | 3/2008 | Colliou et al. |
| 2007/0043345 A1 | 2/2007 | Davalos et al. | | 2008/0071264 A1 | 3/2008 | Azure |
| 2007/0049800 A1 | 3/2007 | Boulais | | 2008/0086172 A1 | 4/2008 | Martin et al. |
| 2007/0049902 A1 | 3/2007 | Griffin et al. | | 2008/0097159 A1 | 4/2008 | Ishiguro |
| 2007/0051375 A1 | 3/2007 | Milliman | | 2008/0097472 A1 | 4/2008 | Agmon et al. |
| 2007/0060880 A1 | 3/2007 | Gregorich et al. | | 2008/0097483 A1 | 4/2008 | Ortiz et al. |
| 2007/0067017 A1 | 3/2007 | Trapp | | 2008/0103527 A1 | 5/2008 | Martin et al. |
| 2007/0073102 A1 | 3/2007 | Matsuno et al. | | 2008/0114384 A1 | 5/2008 | Chang et al. |
| 2007/0073269 A1 | 3/2007 | Becker | | 2008/0119870 A1 | 5/2008 | Williams |
| 2007/0079924 A1 | 4/2007 | Saadat et al. | | 2008/0119891 A1 | 5/2008 | Miles et al. |
| 2007/0088370 A1 | 4/2007 | Kahle et al. | | 2008/0125796 A1 | 5/2008 | Graham |
| 2007/0100375 A1 | 5/2007 | Mikkaichi et al. | | 2008/0132892 A1 | 6/2008 | Lunsford et al. |
| 2007/0100376 A1 | 5/2007 | Mikkaichi et al. | | 2008/0139882 A1 | 6/2008 | Fujimori |
| 2007/0106118 A1 | 5/2007 | Moriyama | | 2008/0147113 A1 | 6/2008 | Nobis et al. |
| 2007/0112251 A1 | 5/2007 | Nakhuda | | 2008/0171907 A1 | 7/2008 | Long et al. |
| 2007/0112331 A1 | 5/2007 | Weber et al. | | 2008/0177135 A1 | 7/2008 | Muyari et al. |
| 2007/0112342 A1 | 5/2007 | Pearson et al. | | 2008/0188868 A1 | 8/2008 | Weitzner et al. |
| 2007/0112383 A1 | 5/2007 | Conlon et al. | | 2008/0200755 A1 | 8/2008 | Bakos |
| 2007/0112384 A1 | 5/2007 | Conlon et al. | | 2008/0200762 A1 | 8/2008 | Stokes et al. |
| 2007/0112385 A1 | 5/2007 | Conlon | | 2008/0200911 A1 | 8/2008 | Long |
| 2007/0112417 A1 | 5/2007 | Shanley et al. | | 2008/0200912 A1 | 8/2008 | Long |
| 2007/0112425 A1 | 5/2007 | Schaller et al. | | 2008/0200933 A1 | 8/2008 | Bakos et al. |
| 2007/0118115 A1 | 5/2007 | Artale et al. | | 2008/0200934 A1 | 8/2008 | Fox |
| 2007/0123840 A1 | 5/2007 | Cox | | 2008/0208213 A1 | 8/2008 | Benjamin et al. |
| 2007/0129605 A1 | 6/2007 | Schaaf | | 2008/0221587 A1 | 9/2008 | Schwartz |
| 2007/0129719 A1 | 6/2007 | Kendale et al. | | 2008/0221619 A1 | 9/2008 | Spivey et al. |
| 2007/0129760 A1 | 6/2007 | Demarais et al. | | 2008/0228213 A1 | 9/2008 | Blakeney et al. |
| 2007/0135709 A1 | 6/2007 | Rioux et al. | | 2008/0230972 A1 | 9/2008 | Ganley |
| 2007/0135803 A1 | 6/2007 | Belson | | 2008/0234696 A1 | 9/2008 | Taylor et al. |
| 2007/0142706 A1 | 6/2007 | Matsui et al. | | 2008/0243106 A1 | 10/2008 | Coe et al. |
| 2007/0142780 A1 | 6/2007 | Van Lue | | 2008/0243148 A1 | 10/2008 | Mikkaichi et al. |
| 2007/0154460 A1 | 7/2007 | Kraft et al. | | 2008/0243176 A1 | 10/2008 | Weitzner et al. |
| 2007/0156028 A1 | 7/2007 | Van Lue et al. | | 2008/0249567 A1 | 10/2008 | Kaplan |
| 2007/0156127 A1 | 7/2007 | Rioux et al. | | 2008/0262540 A1 | 10/2008 | Bangera et al. |
| 2007/0161855 A1 | 7/2007 | Mikkaichi et al. | | 2008/0269782 A1 | 10/2008 | Stefanchik et al. |
| 2007/0162101 A1 | 7/2007 | Burgermeister et al. | | 2008/0269783 A1 | 10/2008 | Griffith |
| 2007/0173691 A1 | 7/2007 | Yokoi et al. | | 2008/0275474 A1 | 11/2008 | Martin et al. |
| 2007/0173869 A1 | 7/2007 | Gannoe et al. | | 2008/0275475 A1 | 11/2008 | Schwemberger et al. |
| 2007/0173870 A2 | 7/2007 | Zacharias | | 2008/0287737 A1 | 11/2008 | Dejima |
| 2007/0173872 A1 | 7/2007 | Neuenfeldt | | 2008/0287983 A1 | 11/2008 | Smith et al. |
| 2007/0179525 A1 | 8/2007 | Frecker et al. | | 2008/0300461 A1 | 12/2008 | Shaw et al. |
| 2007/0179530 A1 | 8/2007 | Tieu et al. | | 2008/0300547 A1 | 12/2008 | Bakos |
| 2007/0197865 A1 | 8/2007 | Miyake et al. | | 2008/0309758 A1 | 12/2008 | Karasawa et al. |
| 2007/0198057 A1 | 8/2007 | Gelbart et al. | | 2008/0312496 A1 | 12/2008 | Zwolinski |
| 2007/0203487 A1 | 8/2007 | Sugita | | 2008/0312499 A1 | 12/2008 | Handa et al. |
| 2007/0208336 A1 | 9/2007 | Kim et al. | | 2008/0312500 A1 | 12/2008 | Asada et al. |
| 2007/0208364 A1 | 9/2007 | Smith et al. | | 2008/0312506 A1 | 12/2008 | Spivey et al. |
| 2007/0213754 A1 | 9/2007 | Mikkaichi et al. | | 2008/0319436 A1 | 12/2008 | Daniel et al. |
| 2007/0225554 A1 | 9/2007 | Maseda et al. | | 2008/0319439 A1 | 12/2008 | Ootsubu |
| 2007/0233040 A1 | 10/2007 | Macnamara et al. | | 2009/0054728 A1 | 2/2009 | Trusty |
| 2007/0244358 A1 | 10/2007 | Lee | | 2009/0062788 A1 | 3/2009 | Long et al. |
| 2007/0250038 A1 | 10/2007 | Boulais | | 2009/0062792 A1 | 3/2009 | Vakharia et al. |
| 2007/0250057 A1 | 10/2007 | Nobis et al. | | 2009/0062795 A1 | 3/2009 | Vakharia et al. |
| 2007/0255096 A1 | 11/2007 | Stefanchik et al. | | 2009/0069634 A1 | 3/2009 | Larkin |
| 2007/0255100 A1 | 11/2007 | Barlow et al. | | 2009/0076499 A1 | 3/2009 | Azure |
| 2007/0255273 A1 | 11/2007 | Fernandez et al. | | 2009/0078736 A1 | 3/2009 | Van Lue |
| 2007/0255303 A1 | 11/2007 | Bakos et al. | | 2009/0082776 A1 | 3/2009 | Cresina |
| 2007/0255306 A1 | 11/2007 | Conlon et al. | | 2009/0082779 A1 | 3/2009 | Nakao |
| 2007/0260112 A1 | 11/2007 | Rahmani | | 2009/0112059 A1 | 4/2009 | Nobis |
| 2007/0260117 A1 | 11/2007 | Zwolinski et al. | | 2009/0112062 A1 | 4/2009 | Bakos |
| 2007/0260121 A1 | 11/2007 | Bakos et al. | | 2009/0112063 A1 | 4/2009 | Bakos et al. |
| 2007/0260273 A1 | 11/2007 | Cropper et al. | | 2009/0125042 A1 | 5/2009 | Mouw |
| 2007/0270629 A1 | 11/2007 | Charles | | 2009/0131751 A1 | 5/2009 | Spivey et al. |
| 2007/0270889 A1 | 11/2007 | Conlon et al. | | 2009/0131932 A1 | 5/2009 | Vakharia et al. |

| | | |
|---|---|---|
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0216248 A1 | 8/2009 | Uenohara et al. |
| 2009/0227828 A1 | 9/2009 | Swain et al. |
| 2009/0248055 A1 | 10/2009 | Spivey et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Splvey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198248 A1 | 8/2010 | Vakharia |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0245619 A1 | 10/2011 | Holcomb |
| 2011/0306971 A1 | 12/2011 | Long |
| 2012/0004502 A1 | 1/2012 | Weitzner et al. |
| 2012/0088965 A1 | 4/2012 | Stokes et al. |
| 2012/0089089 A1 | 4/2012 | Swain et al. |
| 2012/0089093 A1 | 4/2012 | Trusty |

FOREIGN PATENT DOCUMENTS

| | | |
|---|---|---|
| DE | 3008120 A1 | 9/1980 |
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |

| | | |
|---|---|---|
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL:http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ECRP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).

U.S. Appl. No. 12/019,461, filed Jan. 24, 2008.
U.S. Appl. No. 12/045,318, filed Mar. 10, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/234,425, filed Sep. 19, 2008.
U.S. Appl. No. 12/060,601, filed Apr. 1, 2008.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Muller et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al,, "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
U.S. Appl. No. 13/036,895, filed Feb. 28, 2011.
U.S. Appl. No. 13/036,908, filed Feb. 28, 2011.
U.S. Appl. No. 13/218,221, filed Aug. 25, 2011.
U.S. Appl. No. 13/267,251, filed Oct. 6, 2011.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
U.S. Appl. No. 13/425,103, filed Mar. 20, 2012.

* cited by examiner

OVERTUBE WITH EXPANDABLE TIP

BACKGROUND

Endoscopy refers to looking inside the human body for medical reasons. Endoscopy may be performed using an instrument called an endoscope. Endoscopy is a minimally invasive diagnostic medical procedure used to evaluate the interior surfaces of an organ by inserting a small tube into the body, often, but not necessarily, through a natural body opening or through a relatively small incision. Through the endoscope, an operator may observe surface conditions of the organs, including abnormal or diseased tissue such as lesions and other surface conditions. The endoscope may have a rigid or a flexible tube and, in addition to providing an image for visual inspection and photography, the endoscope may be adapted and configured for taking biopsies, retrieving foreign objects, and introducing medical instruments to a tissue treatment region referred to as the work site. Endoscopy is a vehicle for minimally invasive surgery.

Laparoscopic surgery is a minimally invasive surgical technique in which operations are performed through small incisions (usually 0.5-1.5 cm), keyholes, as compared to larger incisions needed in traditional open-type surgical procedures. Laparoscopic surgery includes operations within the abdominal or pelvic cavities, whereas keyhole surgery performed on the thoracic or chest cavity is called thoracoscopic surgery. Laparoscopic and thoracoscopic surgery belong to the broader field of endoscopy.

A key element in laparoscopic surgery is the use of a laparoscope: a telescopic rod lens system that is usually connected to a video camera (single-chip or three-chip). Also attached is a fiber-optic cable system connected to a "cold" light source (halogen or xenon) to illuminate the operative field, inserted through a 5 mm or 10 mm cannula to view the operative field. The abdomen is usually insufflated with carbon dioxide gas to create a working and viewing space. The abdomen is essentially blown up like a balloon (insufflated), elevating the abdominal wall above the internal organs like a dome. Carbon dioxide gas is used because it is common to the human body and can be removed by the respiratory system if it is absorbed through tissue.

Minimally invasive therapeutic procedures to treat diseased tissue by introducing medical instruments to a tissue treatment region through a natural opening of the patient are known as Natural Orifice Translumenal Endoscopic Surgery (NOTES)™. In general, there are a variety of systems for inserting an endoscope through a natural opening in the human body, dissecting a lumen, and then, treating the inside of the abdominal cavity. For example, in U.S. Pat. No. 5,297,536, which is incorporated by reference herein, a sample treatment system is disclosed. This system is comprised of a dissecting device for perforating a lumen wall; an endoscope insert member for inserting an endoscope, a tube, an endoscope, and a pneumoperitoneum device for deflating the abdominal cavity; and a closing device.

When transluminal endoscopic surgery is carried out using this system, an endoscope insert member and overtube are first inserted through a natural opening in the human body (mouth, anus, or vagina, for example). The overtube may be absorbed to a required organ wall by vacuum pressure, thus being fixed thereon. An incising instrument may be passed through the overtube, or through the working channel of the endoscope, to form a perforation through the surface of the organ wall. An inflation device, such as a balloon, may be placed in the incision and inflated to radially expand the incision. Once the incision has been enlarged, the overtube then may be inserted through the organ wall to serve as a working channel for the endoscope and other tools. After surgery of the inside of the abdominal cavity is complete, the overtube may be removed from the enlarged incision, the perforation in the organ wall may be closed by an O-ring, and the endoscope and overtube may be withdrawn from the body.

In various known techniques, difficulties may arise when inserting the overtube through the organ wall or other tissue. For example, the organ wall may catch or snag at the interface between the distal end of the tube and the inflation device. Such interference with the organ wall may impede the smooth entry of the overtube through the organ wall. Accordingly, in the field of endoscopy, there remains a need for improved methods and devices for inserting an overtube through a tissue wall during an endoscopic surgical procedure.

FIGURES

The novel features of the various embodiments are set forth with particularity in the appended claims. The various embodiments, however, both as to organization and methods of operation may best be understood by reference to the following description, taken in conjunction with the accompanying drawings as follows.

DESCRIPTION

It will be appreciated that the terms "proximal" and "distal" are used herein with reference to a clinician or user manipulating one end of an instrument that protrudes out of a natural orifice (or opening) of the patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the drawings. However, surgical instruments may be used in many orientations and positions, and these terms are not intended to be limiting and absolute.

During the course of various surgical procedures, especially in intraluminal and transluminal procedures, there often exists a need to create a surgical space for advancing overtubes and surgical instruments or for allowing a surgeon to access a surgical site or work site, for example. Expandable balloons may be used to create a surgical space in advance of the surgical instrument. For example, a small needle (such as a Veress needle) or guidewire that can be first introduced through an organ wall, for example. A deflated balloon can then be introduced into the hole or incision created by the advancing needle or guidewire. As the balloon is transitioned from a deflated or collapsed position to an inflated or expanded position, the balloon can displace the adjacent tissue, creating a surgical space capable of receiving the advancing overtube and/or other surgical instruments.

Figure 1:
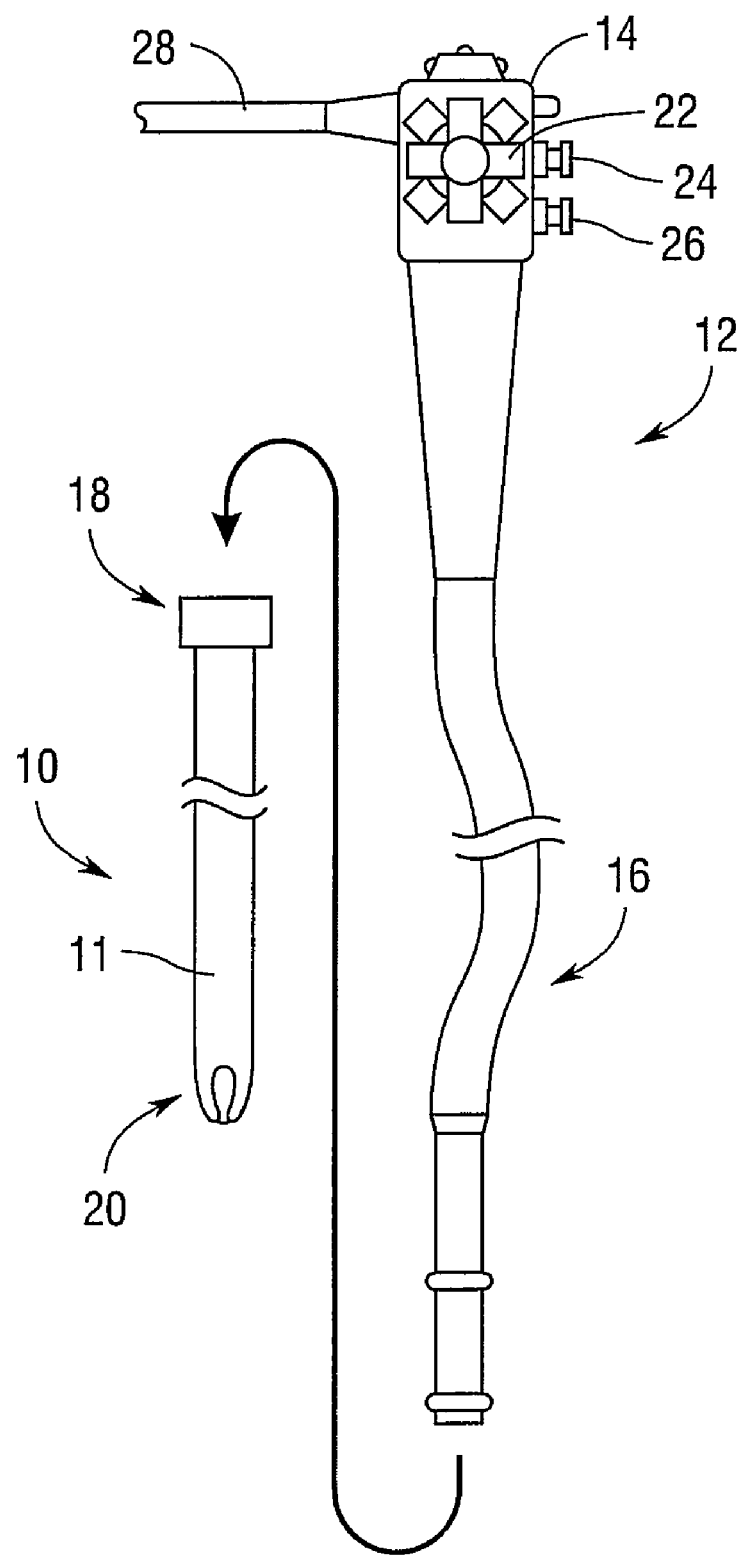
FIG. 1 illustrates one embodiment of endoscopic system and an overtube.

FIG. 1 illustrates one embodiment of an overtube 10. The overtube 10 is generally flexible so as to allow navigation through the tortuous pathway of a body lumen during an endoscopic procedure. The size of the overtube 10 can vary, but in various embodiments it has a length that allows it to be inserted translumenally, such as through a patient's esophagus, and the diameter of its inner lumen allows an endoscope to be received therein. The overtube 10 can be made flexible using various techniques. For example, the overtube 10 can be formed from a flexible material, and/or it can include one or more features formed therein to facilitate flexibility, such as a plurality of cut-outs or slots. In other embodiments, the overtube 10 can be formed from a plurality of linkages that are movably coupled to one another. The overtube 10 can also include regions that vary in flexibility. For example, certain portions of the overtube 10, such as the distal portion, can be more rigid than other portions of the overtube 10, such as the proximal portion, to correspond to the shape of a body lumen through which the overtube 10 is being inserted. This can be achieved by forming the overtube 10 from different materials, varying the diameter or thickness of the overtube 10, or using various other techniques know in the art. A person skilled in the art will appreciate that the overtube 10 can have virtually any configuration that allows the overtube 10 to flex as it is inserted through a tortuous body lumen. The overtube 10 can also include other features to facilitate use, such as one or more spiral wires embedded therein and configuration to preventing kinking of the overtube 10 during flexure.

Still referring to FIG. 1, an endoscopic system 12 may be used with the overtube 10. The endoscopic system 12 may be comprised of a control unit 14 and an insertion portion 16. As illustrated, the insertion portion 16 may be inserted into the proximal end 18 of the overtube 10. The insertion portion 16 may be inserted through an inner lumen 13 (FIG. 2A) extending the length of the overtube 10. The distal end of the insertion portion 16 may extend distally from a distal end 20 of the overtube 10. It is appreciated that other tools and instruments may be inserted into the proximal end 18 of the overtube 10 and extend distally from the proximal end 18 of the overtube 10. Additionally, as may be readily understood by those skilled in the art, various tools and instruments may be inserted through various working channels or lumens internal to the insertion portion 16 of the endoscopic system 12.

The control unit 14 of the endoscopic system 12 may comprise a control knob 22 for manipulating or bending the insertion portion 16. An air/water feed button 24 and a suction button 26 may be arranged on the side of the control unit 14. A cord 28 may be coupled to the control unit 14. As appreciated by those skilled in the art, various embodiments of the control unit 14 may have different configurations with different functionality. Furthermore, as may be readily appreciated, the control unit 14 may be configured for manual control by a clinician (as shown in FIG. 1) or configured for other types of control, such as electronic or motorized, for example.

In one embodiment, the overtube 10 may be employed in conjunction with a flexible endoscope, such as the GIF-100 model available from Olympus Corporation. The flexible endoscope may be introduced into the patient trans-anally through the colon, orally through the esophagus, vaginally through the uterus, or the abdomen via an incision or keyhole and an overtube, for example. The endoscope assists the surgeon to guide and position surgical devices near the tissue treatment region or target site to treat diseased or damaged tissue in various body lumens and organs such as the abdomen, esophagus, stomach, colon, liver, breast, brain, lung, and other internal tissue treatment regions.

Figure 2A:
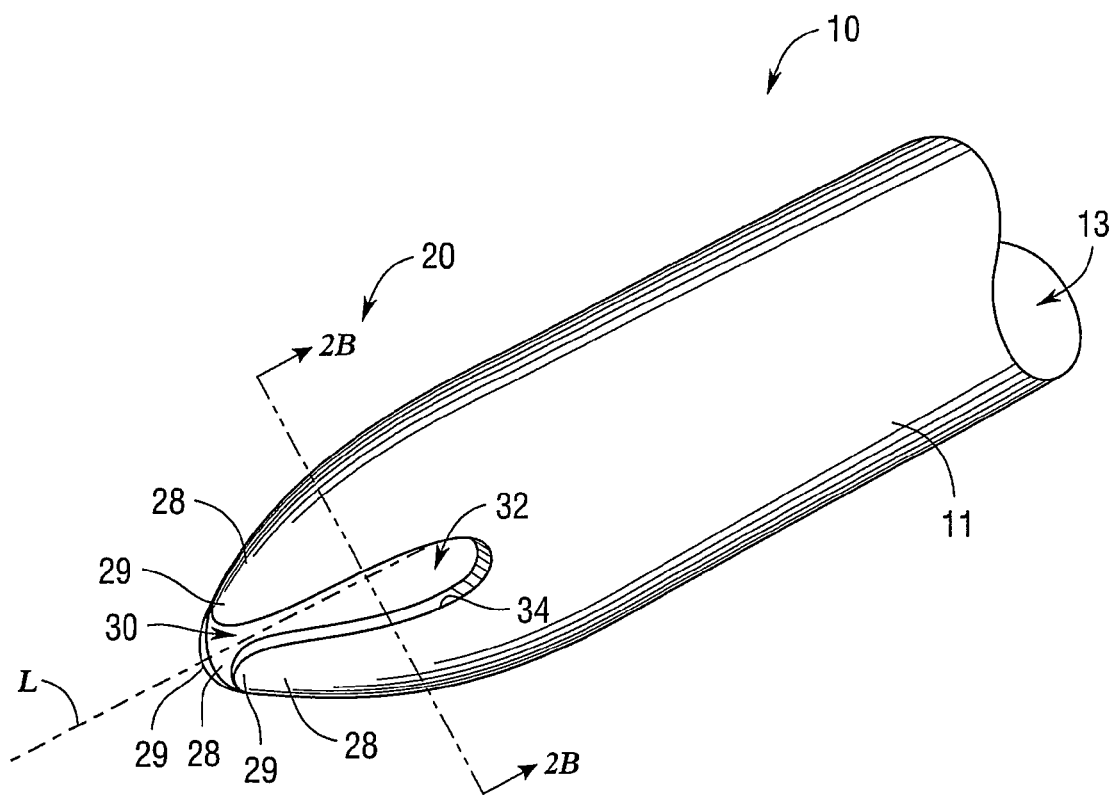
FIG. 2A illustrates one embodiment of the distal tip of the overtube shown in FIG. 1.

An embodiment of the distal end 20 of the overtube 10 is illustrated in FIG. 2A. As shown, the overtube 10 may comprise a body 11 and fingers 28 extending distally from the distal end 20. The fingers 28 may have a thickness determined by a sidewall 34. The sidewall 34 may have uniform thickness (as shown), or, in various embodiments, the thickness of the sidewall 34 may vary. For example, the thickness of the sidewall 34 may decrease toward the distal ends of the fingers 28. The thickness of the sidewall 34 may be substantially similar to sidewall thickness of the body 11, or, in various embodiments the relative thicknesses may differ. The fingers 28 are configured to create a radially expandable tip located on the distal end 20 of the overtube 10. The fingers 28 may slope inwardly toward the longitudinal axis (shown as "L") of the overtube 10 to create a generally tapered distal end. An opening 30 is thereby created by the distal ends of the fingers 28. Each finger 28 may be configured to radially articulate with respect to the longitudinal axis L thereby varying the diameter of the opening 30. In various embodiments the fingers 28 may be each separated by a notch 32. The notches 32 may separate adjacent fingers 28 and may be of any suitable shape, such as substantially a teardrop shape. Similarly, the fingers 28 may be constructed in any suitable shape. For example, ends 29 of the fingers 28 may be generally rounded (as shown in FIG. 2A), or the ends 29 may have other configurations, such as pointed or flat, for example. Furthermore, the fingers 28 may be, for example, transparent, opaque, or a combination of both. The fingers 28 may be biased to a "closed", or first position, shown in FIG. 2A.

Figure 2B:
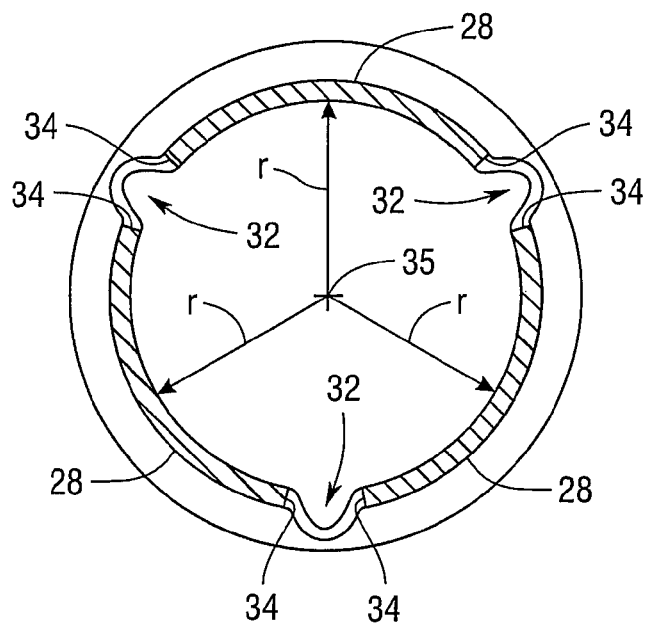
FIG. 2B illustrates a cross-sectional view of the distal tip of the overtube shown in FIG. 2A.

FIG. 2B shows a cross-sectional view of the embodiment of the overtube 10 shown in FIG. 2A. As illustrated, in various embodiments, the profile of fingers 28 may have a curvature defined by a radius "r," which converges on a point 35. In other embodiments, the fingers 28 may have different profiles, including profiles which comprise both flat and curved sections. It may also be appreciated that each finger 28 may have a different profile than other fingers 28.

Figure 2C:
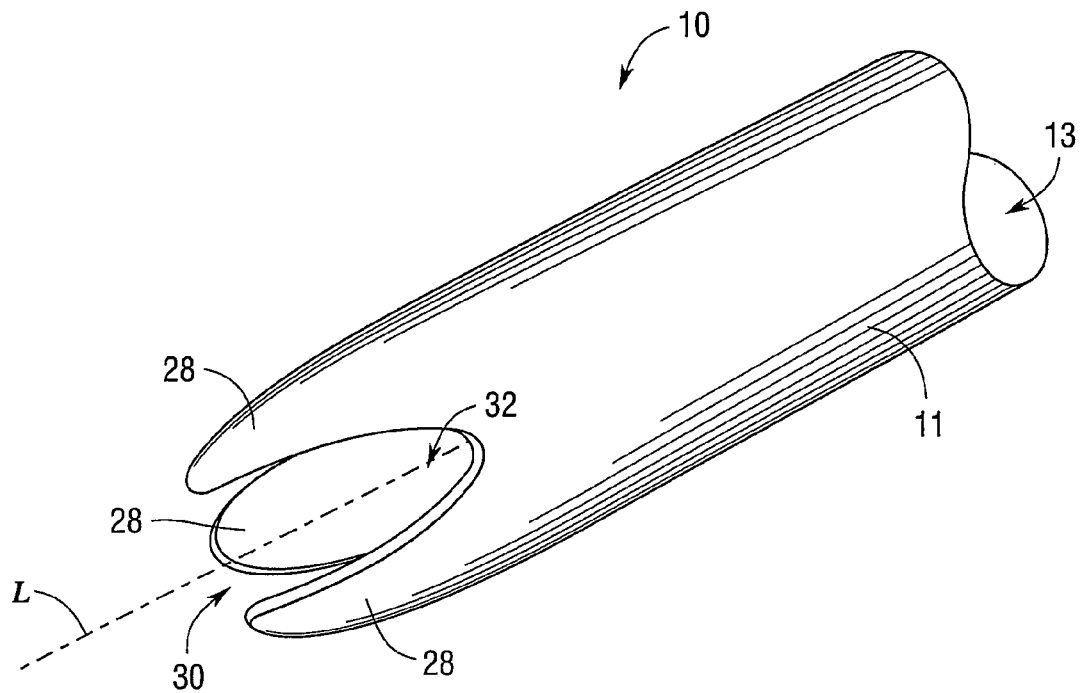
FIG. 2C illustrates one embodiment of the distal tip of the overtube shown in FIG. 1.

Referring now to FIG. 2C, an embodiment of the overtube 10 in an "open", or second position is illustrated. As shown, the fingers 28 are radially articulated or expanded, thereby increasing the opening 30 at the distal end 20 of the overtube 10. In various embodiments, the opening 30 may increase to a diameter up to the diameter of the body 11. As shown in FIG. 2C, as the fingers 28 articulate the notches 32 also change shape and expand to accommodate the articulation of the fingers 28 from the closed position to the open position.

Figure 3:
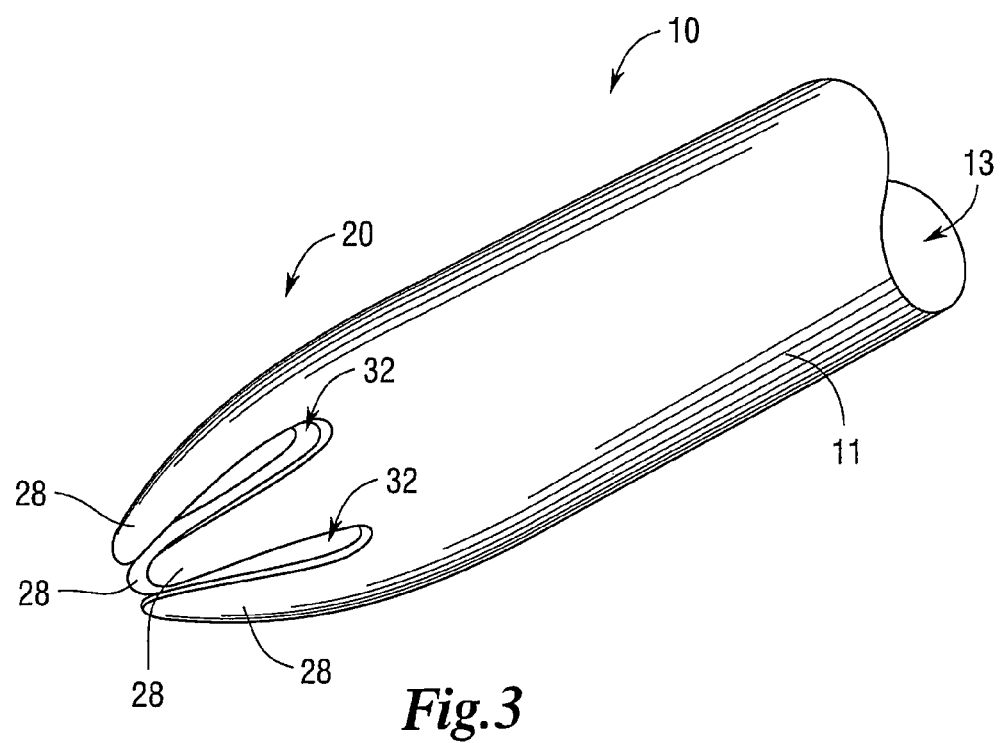
FIG. 3 illustrates one embodiment of the distal tip of an overtube.

In various embodiments the overtube 10 may have any suitable number of fingers or tabs extending from the distal end 20. As shown in FIG. 3, the illustrated embodiment comprises four fingers 28 extending from the distal end 20. In some implementations, the distal end 20 may comprise additional or fewer fingers. In various embodiments, the fingers 28 each may have different dimensions or may be formed in a different shape. In some implementations, a first plurality of fingers 28 may be comprised of a first shape and a second plurality of fingers 28 may be comprised of a second shape. While certain embodiments of the fingers 28 have been disclosed, the configurations of the fingers 28 are not limited to these embodiments. As understood by those skilled in the art, any suitable finger configuration may be used.

Figure 4:
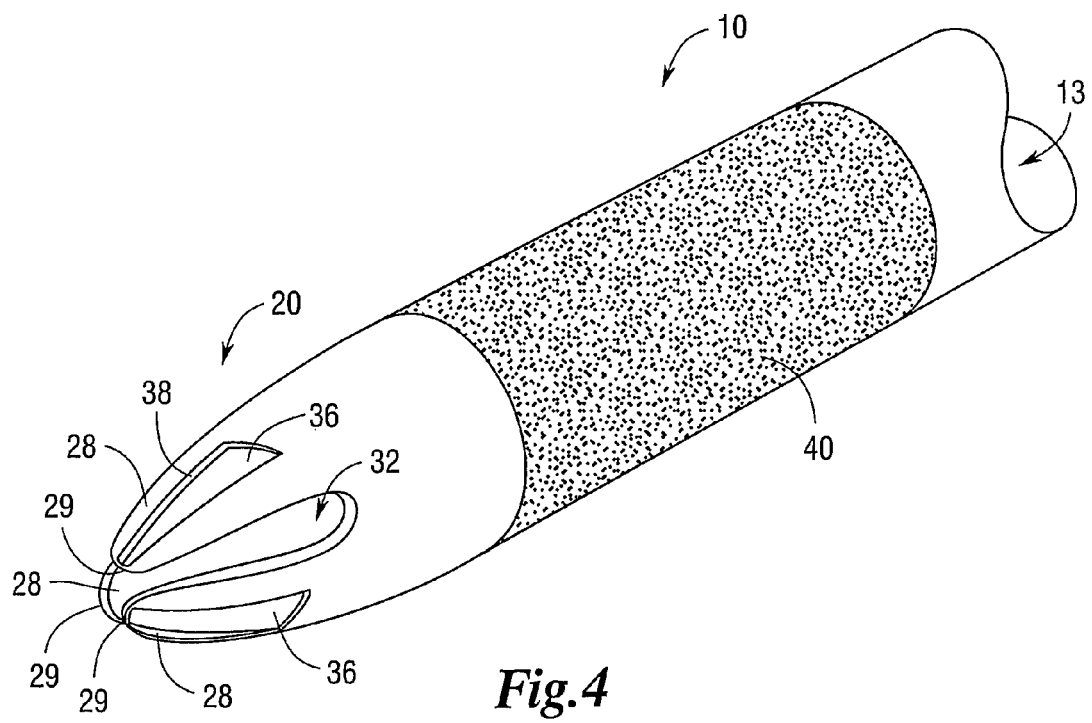
FIG. 4 illustrates one embodiment of the distal tip of an overtube.

As illustrated in FIG. 4, the distal end 20 of the overtube 10 may comprise cutting elements 36 extending from an outer surface of the fingers 28. In some embodiments, the cutting elements 36 may extend substantially perpendicularly from the fingers 28. Each finger 28 may include a cutting element 36, or, in various embodiments, only certain fingers may include a cutting element 36. In other embodiments, the fingers 28 each may include multiple cutting elements 36. The cutting element 36 may include a cutting edge 38. The cutting edge 38 may be sharpened, or otherwise configured to aid in the cutting of tissue during use of the overtube 10. The cutting elements 36 may be formed unitary with the associated fingers 28. Or, in various embodiments, the cutting elements 36 may be fastened to or coupled to the associated fingers 28. The cutting elements 36 may be an integrally formed recess on the exterior surface of the fingers 28. The cutting elements 36 may be configured in any suitable shape. As illustrated, the cutting elements 36 may extend to the distal ends 29 of the fingers 28. In various embodiments, the cutting elements 36 may be coupled to an energy source to aid in the cutting of tissue.

Still referring to FIG. 4, the overtube 10 may include a gripping section 40. The gripping section 40 is configured to assist in keeping the overtube 10 in various orientations during surgical procedures. For example, the gripping section 40 may increase the coefficient of friction between the overtube 10 and the tissue through which the overtube 10 is positioned. The gripping section 40 may be, for example, a series of ribs or otherwise textured surface. In the illustrated embodiment, the gripping section 40 is shown as a band located near the distal end 20 of the overtube 10, however any suitable size and configuration may be used.

Figure 5A:
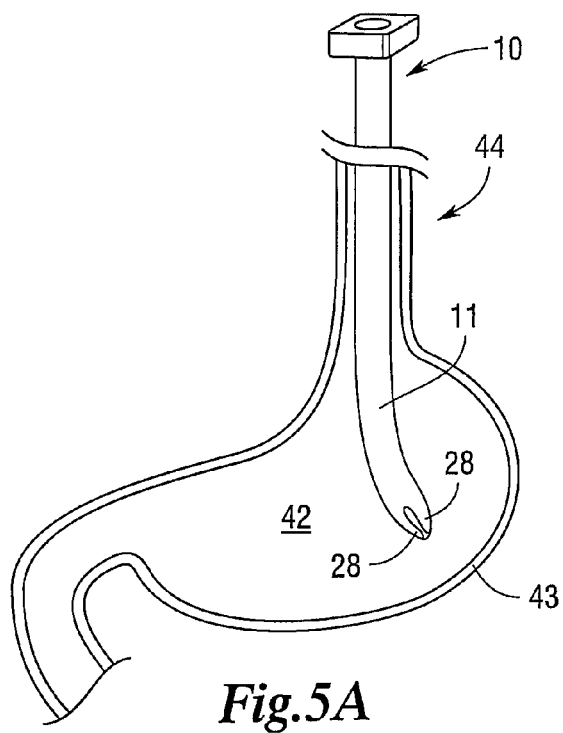
FIGS. 5A-5C show the progression of one embodiment of an overtube during a transluminal procedure using the stomach cavity.
Figure 5B:
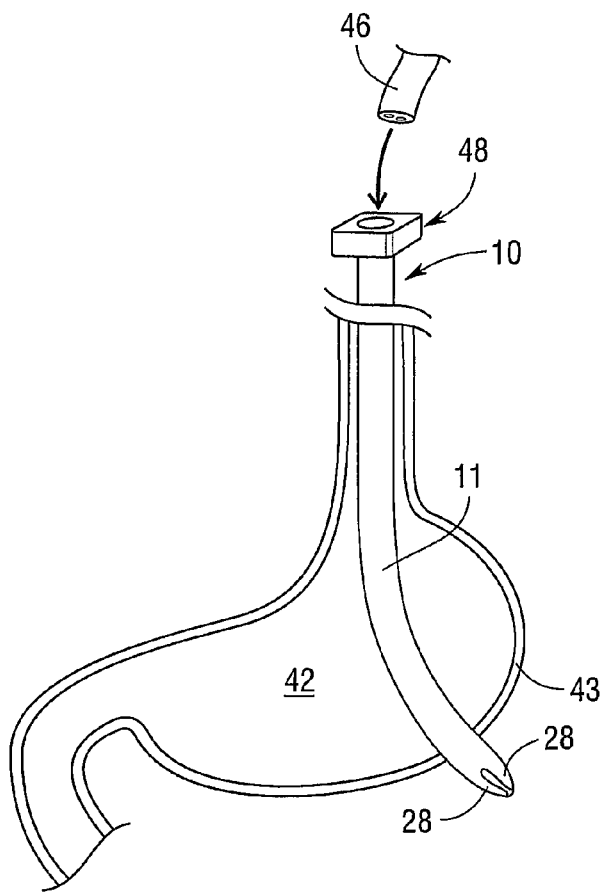
Figure 5C:
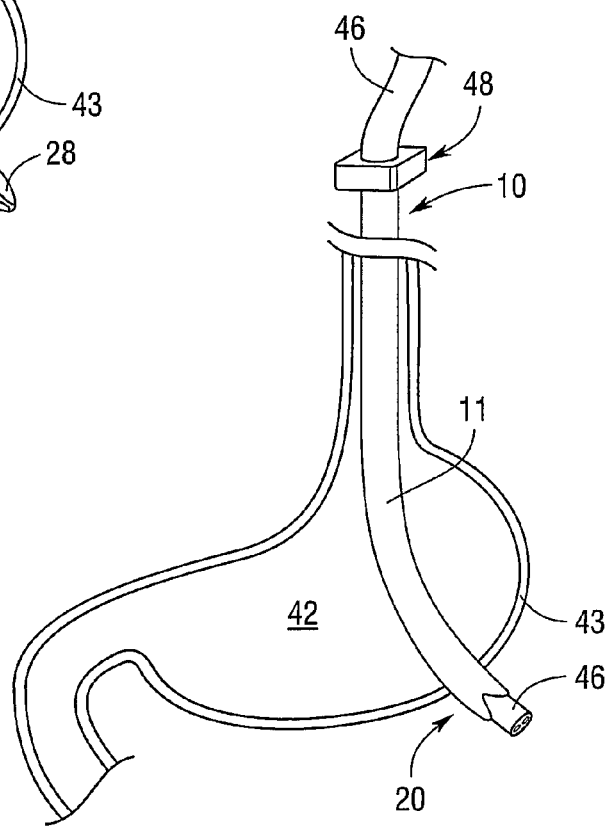

FIGS. 5A-5C illustrate an example use of the overtube 10 during a surgical procedure. Referring first to FIG. 5A, the overtube 10 may be introduced into the stomach cavity 42 through the mouth (not shown) and esophagus 44. It is appreciated that the use of the overtube 10 is not limited to use with the stomach cavity 42. It may be used within any body cavity, such as the uterus, colon, for example. Referring next to FIG. 5B, and as described in more detail below, the overtube 10 may penetrate the stomach wall 43. Once the distal end 20 of overtube 10 has penetrated the stomach wall 43, working tools, such as an endoscope 46 may be inserted into the proximal end 48 of the overtube 10 and fed through the body 11 and ultimately extend from the distal end 20 of the overtube 10 (FIG. 5C). Once in place, the overtube 10 serves as a conduit for a user to feed various tools and components to a working site.

Figure 6A:
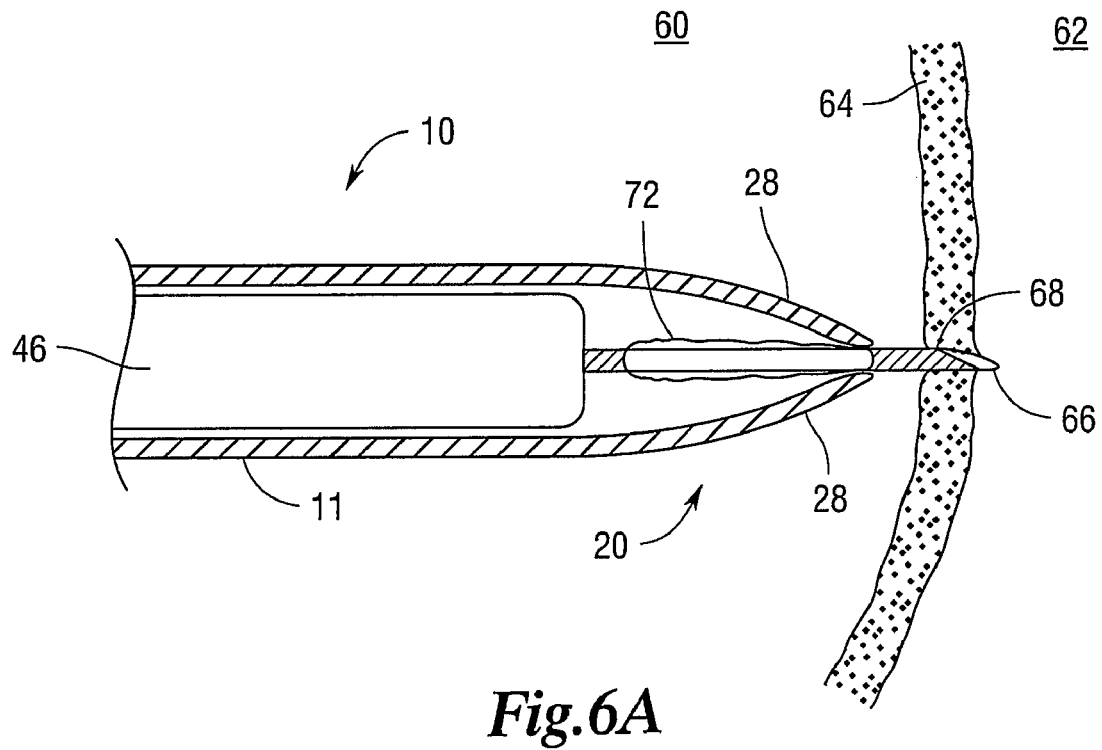
FIGS. 6A-6F show the progression of one embodiment of an overtube penetrating through a tissue wall during a transluminal procedure.
Figure 6B:
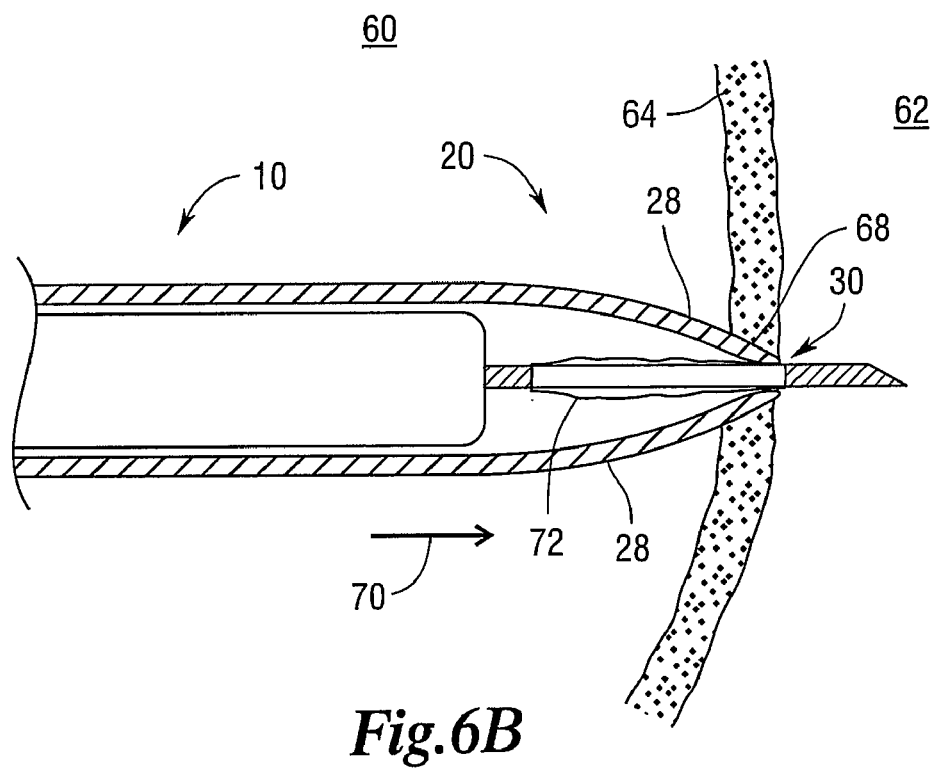

An example penetration of an embodiment of the overtube 10 through tissue is shown in FIGS. 6A-6F. Referring first to FIG. 6A, the overtube 10 is shown positioned within a first body cavity 60. The first body cavity 60 may be, for example, the stomach, colon, or uterus. A second body cavity 62 is illustrated which is separated from the first body cavity 60 by tissue 64. The tissue 64 may be, for example, the stomach wall, colon wall, uterus wall, or other organ or tissue. In order to access the second body cavity 62 with tools, such as an endoscope or graspers, the tissue 64 must be penetrated. In various embodiments, a tool, such as the endoscope 46 is fed down the body 11 of the overtube 10. A needle 66, or other incising device, such as a tubular stylette or guidewire, may be fed through a working channel of the endoscope 46 to make a puncture site 68 in the tissue wall 64. Referring now to FIG. 6B, the distal ends of the fingers 28 may be inserted into the puncture site 68 by the user through longitudinal movement of the overtube 10 in the direction indicated by arrow 70. As illustrated, the distal end 20 is in the "closed", or first position. A deflated balloon 72 associated with the needle 66 also may be advanced into the puncture site 68 such that the fingers 28 are positioned in between the deflated balloon 72 and the tissue wall 64. As illustrated in FIG. 6B, the needle 66 and a portion of the deflated balloon 72 may extend distally from the opening 30 of the overtube 10. In various embodiments, approximately half of the deflated balloon 72 may be positioned in the second cavity 62 through the puncture site 68, with a portion of a proximal portion of the deflated balloon 72 remaining internal to the radially expandable tip of the overtube 10.

Once the distal ends of the fingers 28 have been inserted into the puncture site 68, the puncture site 68 then may be expanded to accommodate the body 11 of the overtube 10. The balloon 72 may be used to expand the puncture site 68. The inflation of the balloon 72 may be controlled via the control unit 14 operated by the user.

Figure 6C:
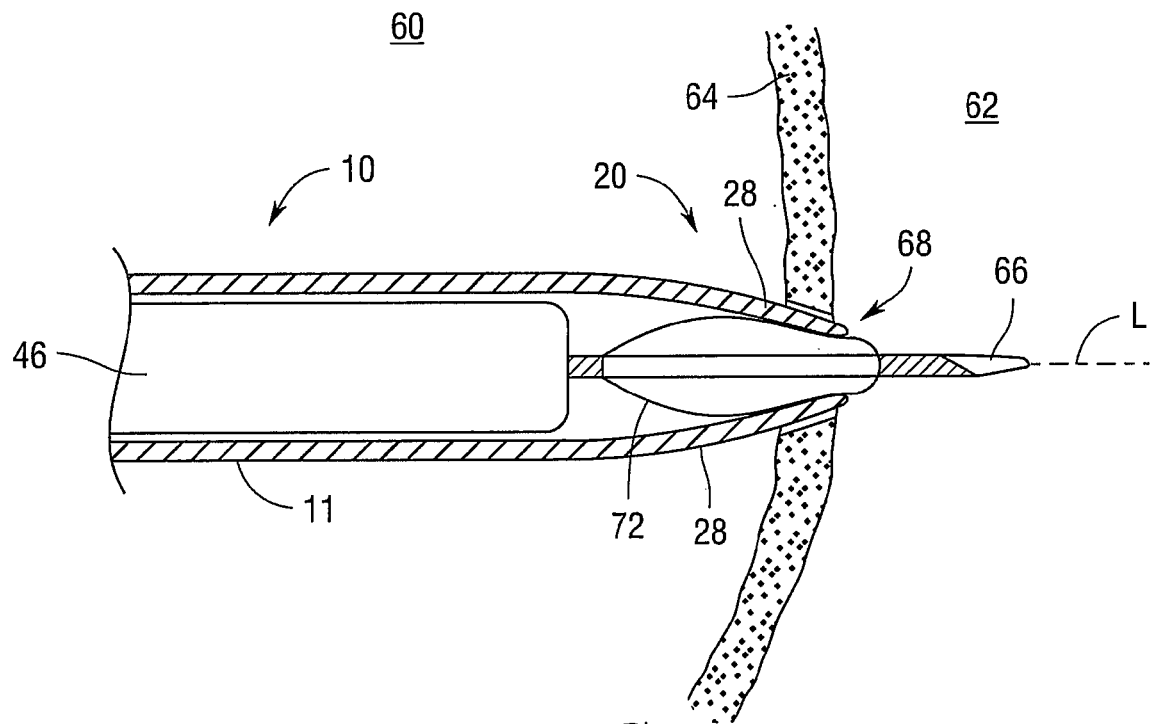

FIG. 6C illustrates one embodiment of the overtube 10 and the balloon 72 when the balloon 72 is partially inflated with a fluid, such as saline or carbon dioxide, for example. As illustrated, the inflation of balloon 72 forces the fingers 28 to articulate or expand radially with respect to the longitudinal axis L. As the fingers 28 articulate radially, the circumferential tissue at the puncture site 68 is enlarged or dilated. In various embodiments, cutting elements 32 (FIG. 3) may be used to assist in the dilation.

Figure 6D:
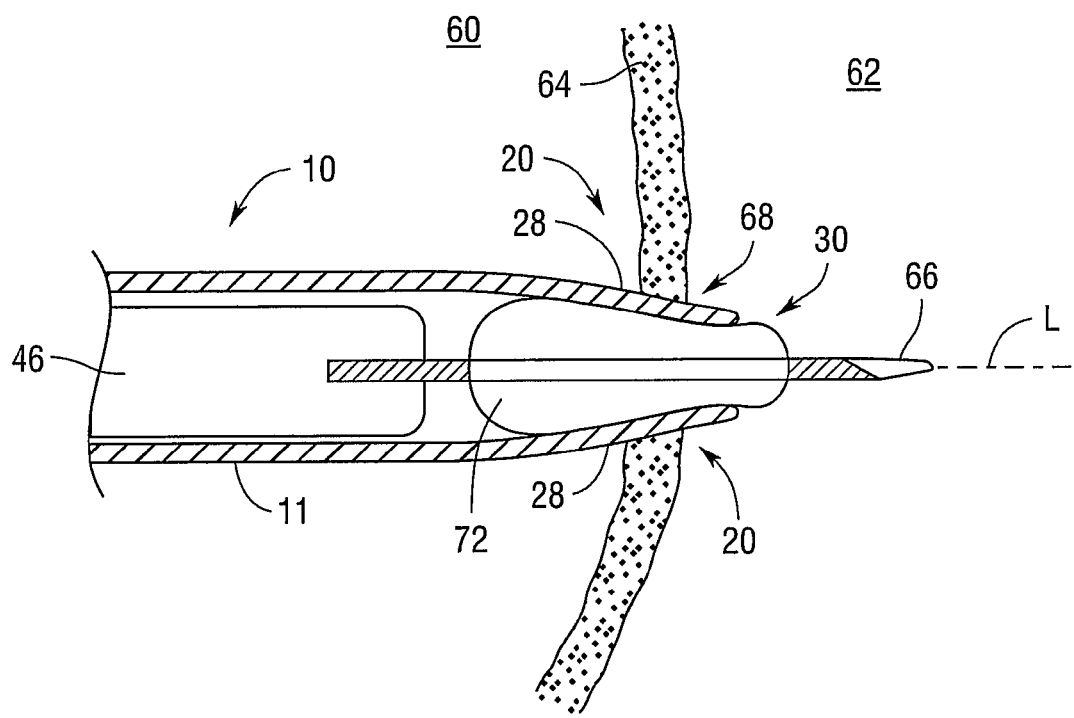

FIG. 6D illustrates one embodiment of the overtube 10 and the balloon 72 when the balloon 72 is nearly fully inflated with the fluid. As illustrated, the further inflation of balloon 72 by the user forces the fingers 28 to articulate radially with respect to the longitudinal axis L. As the fingers 28 articulate radially, the opening 30 at the distal end 20 of the overtube 10 continues to enlarge or dilate.

Figure 6E:
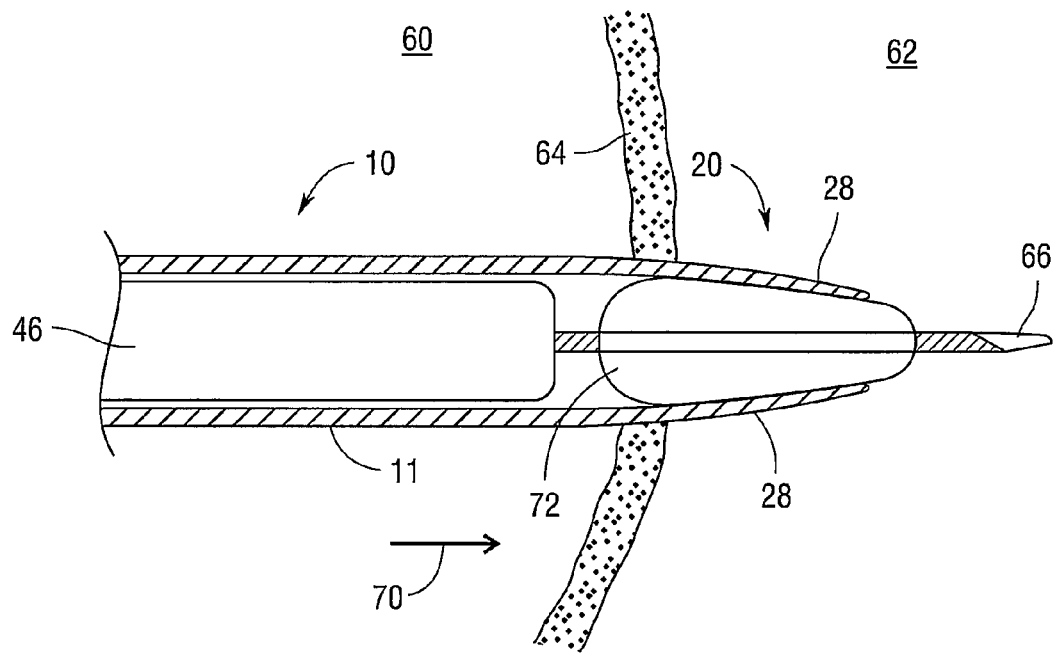

FIG. 6E illustrates one embodiment of the overtube 10 and the balloon 72 when the balloon 72 is inflated with the fluid to nearly fully articulate or expand the fingers 28. As illustrated, once the fingers are nearly fully articulated, the puncture site 68 in the tissue wall 64 is nearly the same diameter as the body 11. Once the puncture site 68 is expanded by the articulating fingers 28, the overtube 10 may be advanced in the direction indicated by arrow 70 to pass into the second body cavity 62.

Figure 6F:
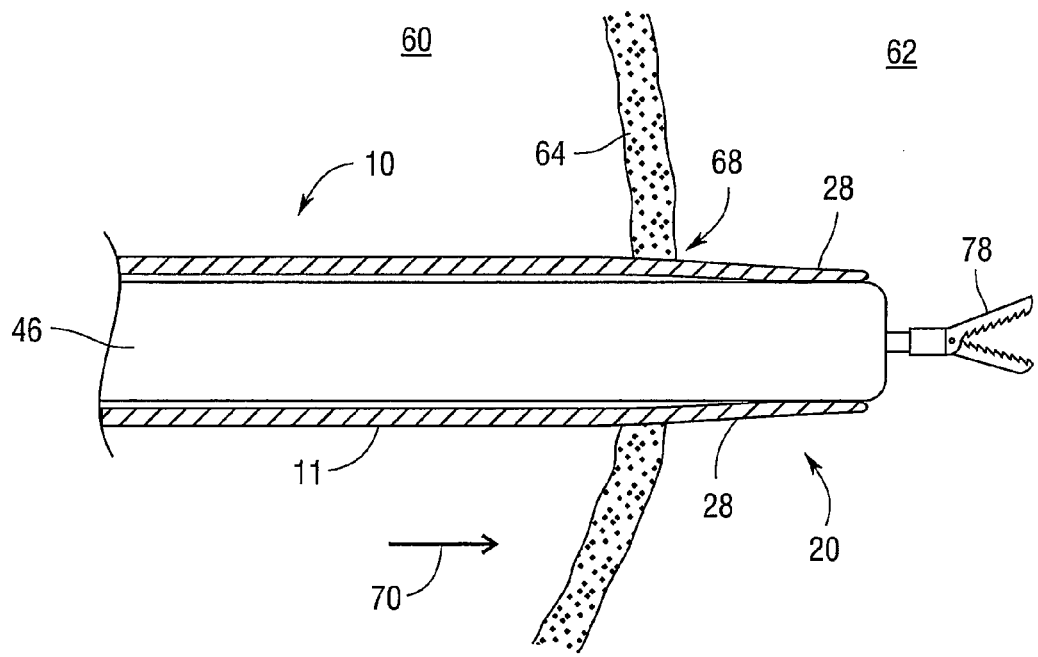

FIG. 6F illustrates one embodiment of the overtube 10 accessing the second body cavity 62. As illustrated, the balloon 72 has been deflated and retracted from the distal end 20 of the overtube 10. The endoscope 46 has been advanced in the direction indicated by arrow 70 to extend distally from the distal end 20 of the overtube 10. As shown in FIG. 6F, the fingers 28 may articulate radially to accommodate the endoscope 46 as it advances distally. Once the second body cavity 62 has been accessed, tools, such as graspers 78 may be deployed by the user to perform the required tasks in the second body cavity 62.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by the cleaning or replacement of particular pieces, and subsequent reassembly. In particular, the device can be disassembled, and any number of the particular pieces or parts of the device can be selectively replaced or removed in any combination. Upon the cleaning and/or replacement of particular parts, the device can be reassembled for subsequent use either at a reconditioning facility or by a surgical team immediately prior to a surgical procedure. Those skilled in the art will appreciate that the reconditioning of a device can utilize a variety of techniques for disassembly, cleaning/replacement, and reassembly. The use of such techniques, and the resulting reconditioned device, are all within the scope of the present application.

Preferably, the various embodiments described herein will be processed before surgery. First, a new or used device is obtained and, if necessary, cleaned. The instrument can then be sterilized. In one sterilization technique, the device is placed in a closed and sealed container, such as a plastic or TYVEK® bag. The container and device are then placed in a field of radiation that can penetrate the container, such as gamma radiation, x-rays, or high-energy electrons. The radiation kills bacteria on the instrument and in the container. The sterilized device can then be stored in the sterile container. The sealed container keeps the instrument sterile until it is opened in the medical facility. It is preferred that the device is sterilized. This can be done by any number of ways known to those skilled in the art, including beta or gamma radiation, ethylene oxide, or steam.

Although the various embodiments have been described herein in connection with certain disclosed embodiments, many modifications and variations to those embodiments may be implemented. Also, where materials are disclosed for certain components, other materials may be used. The foregoing description and following claims are intended to cover all such modifications and variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

I claim:

1. A translumenal overtube device, comprising:
    an elongate flexible overtube comprising a distal end, a proximal end, and a body, wherein the body defines a lumen extending the length of the overtube, and wherein the lumen is dimensioned to receive an insertion portion of an endoscope; and
    a plurality of radially articulating fingers separated by notches projecting from the distal end of the flexible overtube, wherein at least one of the radially articulating fingers comprises an integrally formed cutting element recessed on an exterior surface of the at least one of the radially articulating fingers.

2. The device of claim 1, wherein the radial articulation of the fingers is configured to dilate a tissue opening.

3. The device of claim 2, wherein each finger has a distal end and a proximal end, the distal end forming an expandable opening.

4. The device of claim 3, wherein the expandable opening expands when the plurality of fingers radially articulate.

5. The device of claim 4, wherein the expandable opening is configured to receive a tool therethrough.

6. The device of claim 4, wherein the expandable opening is configured to receive an incising device therethrough.

7. The device of claim 1, wherein the overtube comprises at least a first finger, a second finger, and a third finger.

8. The device of claim 1, wherein the distal end of the overtube has a non-articulated position and an articulated position, wherein the distal end of the overtube is tapered in the non-articulated position.

9. The device of claim 8, wherein a balloon is used to move the distal end from the non-articulated position to the articulated position.

10. The device of claim 1, wherein the cutting element comprises a cutting edge.

11. The device of claim 1, wherein an exterior surface of the overtube comprises a gripping portion configured to assist in keeping the overtube in an orientation during a surgical procedure.

12. The device of claim 11, wherein the gripping portion includes a surface having a higher coefficient of friction than remaining portions of the overtube.

13. The device of claim 12, wherein the surface having a higher coefficient of friction comprises a series of ribs.

14. The device of claim 12, wherein the surface having a higher coefficient of friction comprises a textured surface.

15. A translumenal overtube device, comprising:
    an elongate flexible overtube comprising a distal end, a proximal end, and a body, wherein the body defines a lumen extending the length of the overtube, and wherein the lumen is dimensioned to receive an insertion portion of an endoscope; and
    a plurality of radially articulating fingers separated by notches projecting from the distal end of the flexible overtube, wherein at least one of the plurality of radially articulating fingers comprises an integrally formed cutting element recessed on an exterior surface of the at least one of the radially articulating fingers, wherein the distal end of the overtube has a non-articulated position and an articulated position, wherein the distal end of the overtube is tapered in the non-articulated position, and wherein a balloon is used to move the distal end from the non-articulated position to the articulated position.

16. A translumenal overtube device, comprising:
    an elongate flexible overtube comprising a distal end, a proximal end, and a body, wherein the body defines a lumen extending the length of the overtube, and wherein the lumen is dimensioned to receive an insertion portion of an endoscope, wherein an exterior surface of the overtube comprises a gripping portion configured to assist in keeping the overtube in an orientation during a surgical procedure; and
    a plurality of radially articulating fingers separated by notches projecting from the distal end of the flexible overtube, wherein at least one of the plurality of radially articulating fingers comprises an integrally formed cutting element recessed on an exterior surface of the at least one of the radially articulating fingers.

17. A translumenal overtube device, comprising:
    an elongate flexible overtube comprising a distal end, a proximal end, and a body, wherein the body defines a lumen extending the length of the overtube, wherein an exterior surface of the overtube comprises a gripping portion configured to assist in keeping the overtube in an orientation during a surgical procedure, wherein the lumen is dimensioned to receive an insertion portion of an endoscope; and
    a plurality of radially articulating fingers separated by notches projecting from the distal end of the flexible overtube, wherein the distal end of the overtube has a non-articulated position and an articulated position, wherein the distal end of the overtube is tapered in the non-articulated position, and wherein a balloon is used to move the distal end from the non-articulated position to the articulated position, wherein at least one of the plurality of radially articulating fingers comprises an integrally formed cutting element recessed on an exterior surface of the at least one of the radially articulating fingers.

* * * * *